(12) United States Patent
Walter et al.

(10) Patent No.: US 7,595,024 B2
(45) Date of Patent: Sep. 29, 2009

(54) APPARATUS FOR PRODUCING TISSUE ARRAYS

(75) Inventors: Roland Walter, Neulussheim (DE); Rolf Metzner, Dossenheim (DE)

(73) Assignee: Leica Biosystems Nussloch GmbH, Nussloch (DE)

( * ) Notice: Subject to any disclaimer, the term of this patent is extended or adjusted under 35 U.S.C. 154(b) by 384 days.

(21) Appl. No.: 11/468,984

(22) Filed: Aug. 31, 2006

(65) Prior Publication Data

US 2007/0172942 A1    Jul. 26, 2007

(30) Foreign Application Priority Data

Sep. 1, 2005   (DE) .................. 10 2005 041 780
Sep. 1, 2005   (DE) .................. 10 2005 041 781
Sep. 1, 2005   (DE) .................. 10 2005 041 782

(51) Int. Cl.
*G01N 21/00* (2006.01)
*C12M 1/38* (2006.01)
*G01N 31/00* (2006.01)
*C12M 1/00* (2006.01)

(52) U.S. Cl. ................ 422/63; 422/64; 422/65; 422/66; 422/67; 435/286.3; 435/307.1; 435/287.1

(58) Field of Classification Search .............. None
See application file for complete search history.

(56) References Cited

U.S. PATENT DOCUMENTS

| 6,103,518 | A  | 8/2000  | Leighton |
| 6,383,801 | B1 | 5/2002  | Leighton |
| 6,699,710 | B1 | 3/2004  | Kononen et al. |
| 2002/0106626 | A1 | 8/2002 | Muraca |
| 2003/0017446 | A1 | 1/2003 | Chasse et al. |
| 2003/0186353 | A1 | 10/2003 | Erickson et al. |

FOREIGN PATENT DOCUMENTS

WO    WO-00/52132 A1    9/2000

*Primary Examiner*—Jill Warden
*Assistant Examiner*—Neil Turk
(74) *Attorney, Agent, or Firm*—Hodgson Russ LLP

(57) ABSTRACT

An apparatus for producing a tissue array, having at least one donor block (2) that comprises tissue (3) to be investigated, is described. A marked tissue section of the tissue (3) to be investigated is arranged on a specimen slide (22), a hollow needle (5) for removing a sample from the tissue (3) being present. A sighting device (12) is provided for positioning the hollow needle (5) above the donor block (2).

8 Claims, 2 Drawing Sheets

APPARATUS FOR PRODUCING TISSUE ARRAYS

CROSS REFERENCE TO RELATED APPLICATIONS

This application claims priority of German patent application no. 10 2005 041 780.9 filed Sep. 1, 2005, which is incorporated by reference herein. This application also claims priority of German patent application no. 10 2005 041 781.7 filed Sep. 1, 2005 and German patent application no. 10 2005 041 782.5 filed Sep. 1, 2005, both of which are incorporated by reference herein.

FIELD OF THE INVENTION

The invention concerns an apparatus for producing tissue arrays in a paraffin block, such that the block may be sectioned by a microtome to make a specimen slide having an array of tissue samples observable by microscope.

BACKGROUND OF THE INVENTION

Tissue arrays, also called tissue microarrays (TMAs), contain a plurality of different tissue samples in a single receiver block or paraffin block. The receiver block is sectioned in the usual manner with a microtome, and the section is applied onto a specimen slide. The specimen slide then contains a plurality of different tissue samples. Because of the large number of tissue samples on a single specimen slide, it is possible to stain or process all the samples under the same conditions. As a result, even very complex and expensive staining methods, for example those derived from immunohistochemistry (IHC) or in-situ hybridization (ISH) for revealing DNA or RNA, can be applied effectively.

The production of tissue arrays is very time-consuming, however, since a plurality of different samples (up to 1,000) are arranged next to one another in one receiver block. From the various tissue or sample blocks, a tissue core is punched out with a hollow needle and transferred into a correspondingly prepared receiver block.

Before a tissue core is removed from a sample block, the corresponding site on the sample block must be located and marked. It has proven useful for this purpose, in practice, first to produce usual microtome sections from a sample block, apply them onto specimen slides, stain them using a standard method, and have them inspected by a pathologist. The pathologist then selects the sites of interest on the specimen slide, and marks that site directly on the specimen slide.

The laboratory worker producing the tissue arrays then has the task of locating, on the tissue block, the sites marked on the specimen slide, and removing a tissue core at the corresponding sites.

Punched-out portions or paraffin cores are also removed, using a hollow needle, from the receiver block, which as a rule is made of paraffin. The tissue cores are then introduced into the cavity thus created. As mentioned, as many as 1,000 tissue cores—depending on the application—can be arranged to form an array on one paraffin block. From these dimensions alone, it is apparent that the diameter of the tissue cores is less than 1 mm, and reliable and simple transfer of the tissue cores into the punched hole in the paraffin block is therefore possible only with special equipment.

An apparatus for producing a tissue array is known from U.S. Pat. No. 6,103,518. This apparatus is characterized in that the receiver block is arranged in stationary fashion, and possesses a pivotably mounted needle holder for two hollow needles. The needle holder is aligned onto the receiver block by way of an X-Y micrometer displacement device. The two needles—one for punching out the receiver block, the other for removing the tissue core—can be brought alternately into the working position.

For removal of the tissue core from the tissue block, the latter is placed manually, together with a U-shaped frame, above the paraffin block and aligned onto the hollow needle.

With this apparatus, it has proven difficult to locate, on the tissue block, the site marked on the specimen slide, and furthermore to ensure reliable introduction of the tissue core into the paraffin block.

An automated device for producing tissue arrays is known from U.S. Pat. No. 6,383,801 B1. Here both multiple paraffin blocks and multiple tissue blocks are arranged on an X-Y scanning stage. Also provided here are two hollow needles operating independently of one another, of which one makes the punched holes in the paraffin block and the other is responsible for tissue core removal.

This device is very complex and moreover does not solve the problem of easily locating a marked site on the tissue block.

SUMMARY OF THE INVENTION

It is the object of the present invention to improve a manually operating apparatus for producing tissue arrays in such a way that simple location of a specific site on the tissue block, and targeted removal of a tissue core, becomes possible.

The invention is characterized in that a sighting device is provided for positioning the hollow needle above the donor block, and the marked site is determined via the sighting device.

In a development of the invention, the sighting device is joined to a movable arm, and is thus embodied to be arbitrarily movable above the marked site on the specimen slide.

In a further embodiment of the invention, the arm is embodied as a pantograph, the pantograph comprising two scissor arms joined to one another.

In a development of the invention, the scissor arms are embodied in rotatably mounted fashion.

In a further embodiment of the invention, the second scissor arm is joined to a sight holder for the sighting device, so that the sighting device is configured to be freely movable above the donor block by way of the pantograph. A movement of the second scissor arm also results in a synchronous movement of the first scissor arm, so that a position sighted onto on the donor block is transferred directly to the end of the second scissor arm.

In a development of the invention, the sighting device has associated with it a specimen slide holder for receiving the marked specimen slide.

In a further embodiment of the invention, the donor block is arranged on a turntable and can be placed either in a defined position below the first scissor arm or in a defined position below the second scissor arm.

In a development of the invention, the specimen slide holder is arranged in freely positionable fashion above the donor block, thus ensuring congruent alignment of the tissue section on the specimen slide with respect to the donor block and thereby making possible unimpeded sighting onto the marked tissue site.

In a further embodiment of the invention, the hollow needle is arranged on a needle holder and the needle holder is embodied movably, the first scissor arm comprising a receptacle for a punching lever for actuating the hollow needle. As a result of the arrangement of the sighting device on the second scissor arm, the movement is transferred directly to the needle holder and the hollow needle on the first scissor arm, and the tissue site to be removed on the donor block is thus defined.

In a development of the invention, multiple hollow needles, having different diameters, are arranged circularly next to one another on the needle holder, so that differently dimensioned tissue cores can be removed.

BRIEF DESCRIPTION OF THE DRAWINGS

The invention will be explained in more detail with reference to an exemplifying embodiment, with the aid of the schematic drawings in which.

DETAILED DESCRIPTION OF THE INVENTION

Figure 1:
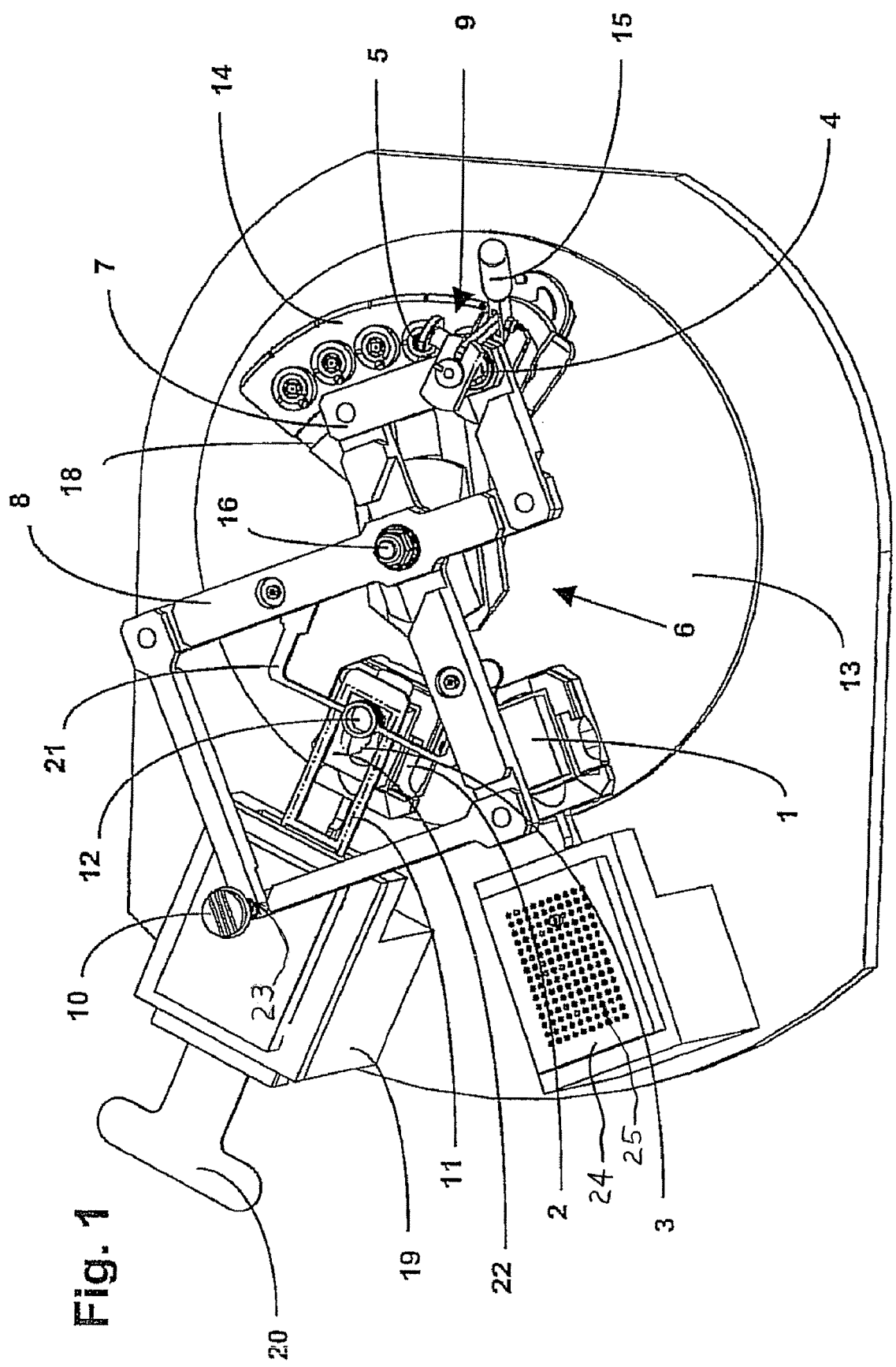
FIG. 1 is a view of the apparatus having the pantograph.

FIG. 1 is a view of the apparatus for producing a tissue array, having a receiver block 1 and a donor block 2 that contains tissue 3 to be investigated. Donor block 2 and receiver block 1 are arranged on a turntable 13. Also provided is a pivotably embodied needle holder 14 that carries a first hollow needle 4 and a second hollow needle 5. First hollow needle 4 serves to create a punched hole in receiver block 1, and second hollow needle 5 is provided in order to remove a tissue core from tissue 3.

The apparatus comprises a pantograph 6, mounted via a rotary shaft 16, having two scissor arms 7 and 8 joined to one another, the end of first scissor arm 7 carrying a receptacle 9 for a punching lever 15 for selectable actuation of first and second hollow needles 4; 5. The end of second scissor arm 8 is equipped with a positioning knob 10 for manual movement of pantograph 6. A detent pin 23 extends downwardly from positioning knob 10 and is operatively associated with a positioning array 24 having an array of individual detent holes 25 for receiving detent pin 23.

The position of positioning knob 10 and detent pin 23 is transferred via the rotatably mounted pantograph 6 to receptacle 9 for punching lever 15. Needle holder 14 is joined in positively engaged fashion (FIG. 2) to first scissor arm 7, and thereby follows the movement of punching lever 15. Selection of the corresponding hollow needle is accomplished by a pivoting motion of needle holder 14 about rotary shaft 16. For punching, receiver block 1 is positioned via turntable 13 below the corresponding first hollow needle 4; first hollow needle 4 is then driven by punching lever 15 into receiver block 1 and makes a punched hole therein.

Also provided is a fixedly arranged slider receptacle 19 for a specimen slide holder 11. Specimen slide holder 11 is arranged movably via a slider 20 in slider receptacle 19, and carries a marked specimen slide 22. Present on specimen slide 22 is a microtome section of donor block 2 having tissue 3.

Donor block 2 is arranged below specimen slide holder 22. By way of the movably mounted specimen slide holder 11, congruency is created between the microtome section and tissue 3 in donor block 2.

A sighting device 12 is arranged on second scissor arm 8 via a sight holder 21. Sighting device 12 is aligned onto the marked site on specimen slide 22 via positioning knob 10. This movement is transferred via pantograph 6 to punching lever 15 and needle holder 14.

Removal of a tissue core from donor block 2 is then performed by the fact that donor block 2 is rotated via turntable 13 out of its position beneath sighting device 12 into a position beneath needle holder 14, and second hollow needle 5 is moved via punching lever 15 into tissue 3 in order to remove a tissue core. Pantograph 6 and sighting device 12 ensure that tissue 3 is removed from the site being sighted onto.

It is of course within the scope of the invention to immobilize the respective positions of the turntable by way of additional detents in order to ensure simple and rapid operation.

Figure 2:
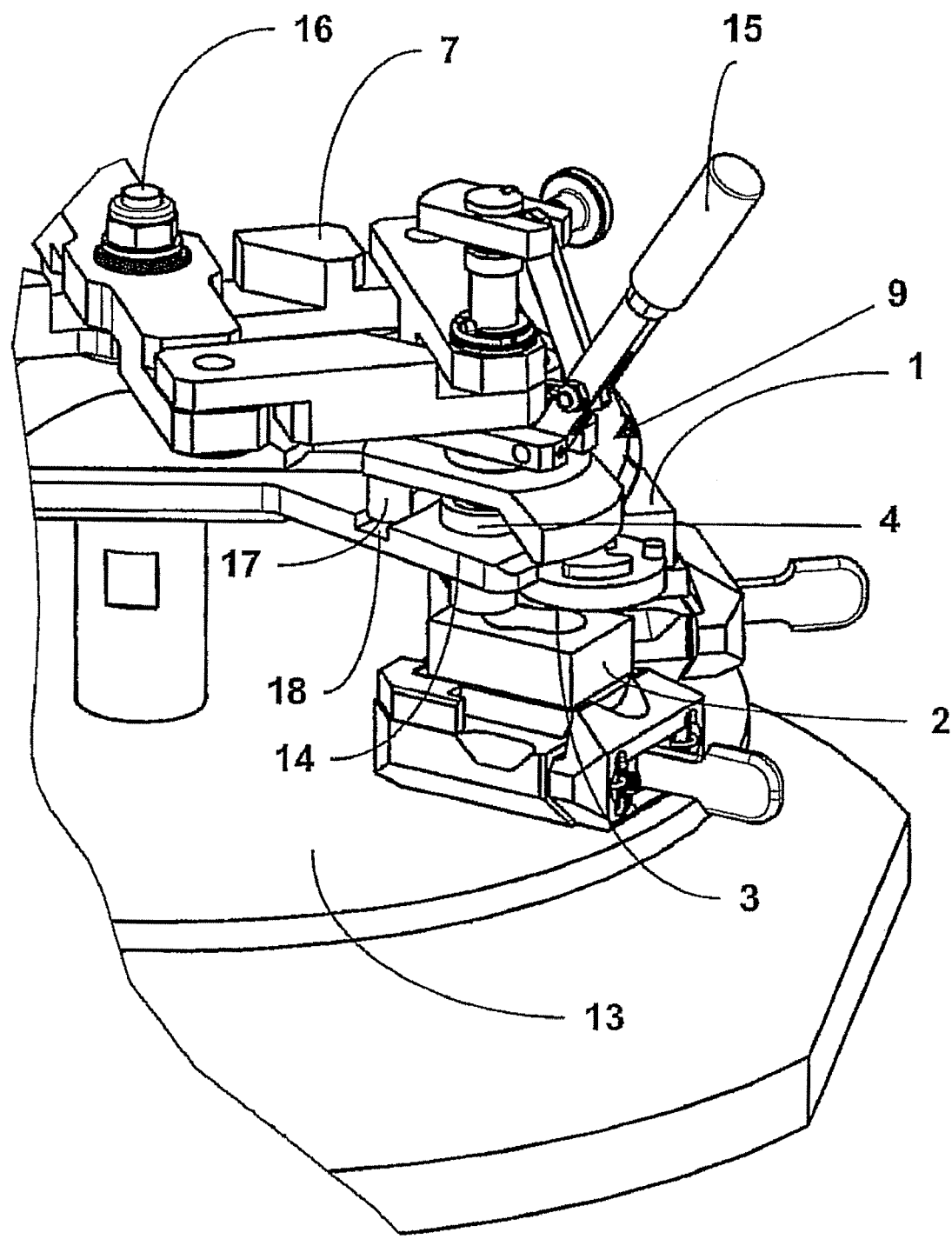
FIG. 2 is a detail view of the apparatus having a needle holder.

FIG. 2 is a detail view of needle holder 14, which is mounted rotatably and displaceably about rotary shaft 16. Needle holder 14 comprises a groove 18 into which a cam 17 positively engages. Cam 17 is joined to first scissor arm 7. A movement of scissor arm 7 is transferred via cam 17 and groove 18 to needle holder 14.

Precise removal of a paraffin core from the receiver block is now described. The position of detent pin 23 on the positioning array 24 is transferred via the rotatably mounted pantograph to receptacle 9 for punching lever 15. As mentioned, needle holder 14 is joined in positively engaged fashion to first scissor arm 7, and thereby follows the movement of punching lever 15. Selection of the corresponding hollow needle is accomplished by pivoting needle holder 14 about rotary shaft 16, positioning receiver block 1 via turntable 13 below the corresponding first hollow needle 4, and driving the first hollow needle 4 into receiver block 1 by operating punching lever 15 to make a punched hole in receiver block 1. Pantograph 6 and positioning array 24 ensure that the positions of first and second hollow needle 4; 5 are precisely maintained. Introduction of the tissue core into the punched hole in receiver block 1 is accomplished in analogous fashion.

PARTS LIST

1 Receiver block, paraffin block
2 Donor block, tissue block
3 Tissue
4 First hollow needle
5 Second hollow needle
6 Pantograph
7 First scissor arm
8 Second scissor arm
9 Receptacle
10 Positioning knob
11 Specimen slide holder
12 Sighting device
13 Turntable
14 Needle holder
15 Punching lever
16 Rotary shaft
17 Cam
18 Groove in 14
19 Slider receptacle
20 Slider
21 Sight holder
22 Specimen slide
23 Detent pin
24 Positioning array
25 Detent holes

What is claimed is:

1. An apparatus comprising:
   a donor block including tissue to be investigate;
   a specimen slide on which is provided a marked tissue section of the tissue to be investigated;
   a hollow needle for removing a sample from the donor block;
   a sighting device alignable with a marked site on the marked tissue section; and a pantograph including a first scissor arm and a second scissor arm joined to one another, the first scissor arm being mechanically connected to the hollow needle, and the second scissor arm having the sighting device arranged thereon and carrying the sighting device above the specimen slide, wherein the pantograph positions the hollow needle relative to the donor block at a position corresponding to an alignment position of the sighting device relative to the marked tissue section.

2. The apparatus according to claim 1, wherein the two scissor arms are rotatably joined to one another.

3. The apparatus according to claim 2, wherein the second scissor arm includes a sight holder for holding the sighting device.

4. The apparatus according to claim 1, further comprising a specimen slide holder for holding the specimen slide, wherein the sighting device is associated with the specimen slide holder.

5. The apparatus according to claim 1, further comprising a turntable, wherein the donor block is arranged on the turntable.

6. The apparatus according to claim 4, wherein the specimen slide holder is adjustably positionable above the donor block.

7. The apparatus according to claim 3, further comprising a movable needle holder for holding the hollow needle and a punching lever for actuating the hollow needle, wherein the first scissor arm includes a receptacle for receiving the punching lever.

8. The apparatus according to claim 7, wherein the needle holder is configured to hold a plurality of hollow needles in a circular arc, the plurality of hollow needles having different diameters.

* * * * *